US012714316B2

(12) United States Patent
Tan et al.

(10) Patent No.: US 12,714,316 B2
(45) Date of Patent: Aug. 25, 2026

(54) NON-CONTACT AND NON-INTRUSIVE CONTINUOUS MONITORING PLATFORM

(71) Applicant: CONEX HEALTHCARE PTE. LTD., Singapore (SG)

(72) Inventors: Swee Yen Tan, Singapore (SG); Nansheng Shen, Singapore (SG); Anshu, Singapore (SG)

(73) Assignee: CONEX HEALTHCARE PTE. LTD., Singapore (SG)

( * ) Notice: Subject to any disclaimer, the term of this patent is extended or adjusted under 35 U.S.C. 154(b) by 672 days.

(21) Appl. No.: 18/041,792

(22) PCT Filed: Aug. 18, 2020

(86) PCT No.: PCT/SG2020/050478

§ 371 (c)(1), (2) Date: Feb. 15, 2023

(87) PCT Pub. No.: WO2022/039663

PCT Pub. Date: Feb. 24, 2022

(65) Prior Publication Data

US 2023/0301522 A1 Sep. 28, 2023

(51) Int. Cl.

*A61B 5/01* (2006.01)
*A61B 5/0205* (2006.01)
*A61B 5/11* (2006.01)

(52) U.S. Cl.

CPC ............ *A61B 5/015* (2013.01); *A61B 5/0205* (2013.01); *A61B 5/1115* (2013.01)

(58) Field of Classification Search

None

See application file for complete search history.

(56) References Cited

U.S. PATENT DOCUMENTS

2019/0349213 A1* 11/2019 Shive .................... G05B 15/02

FOREIGN PATENT DOCUMENTS

| | | | | |
|---|---|---|---|---|
| CN | 103815912 A | | 5/2014 | |
| CN | 105788124 A | | 7/2016 | |
| CN | 108613341 A | | 10/2018 | |
| KR | 20150088135 A | * | 7/2015 | ............ G16H 50/30 |
| WO | 2017098265 A1 | | 6/2017 | |
| WO | 2018136402 A2 | | 7/2018 | |

OTHER PUBLICATIONS

English Translation of CN108613341A (Year: 2018).*

(Continued)

*Primary Examiner* — Jay B Shah

(74) *Attorney, Agent, or Firm* — Mark H. Whittenberger; Holland & Knight LLP

(57) ABSTRACT

This invention relates to a system and method for monitoring a patient. The method comprises obtaining thermal images from a thermal sensor; obtaining respiratory rate and heart rate measurement from an ultra-wideband (UWB) sensor; analysing the thermal images to determine presence of patient on a bed, temperature and activity intensity; and in response to determining presence of patient on the bed and the activity intensity is below a certain threshold, record the temperature, respiratory rate and heart rate.

17 Claims, 5 Drawing Sheets

(56) References Cited

OTHER PUBLICATIONS

Omron—OMRON Develops the World's First* 16×16 Element MEMS Non-Contact Thermal Sensor for Use in Human Presence Sensors Utilizing Wafer-Level Vacuum Packaging Technology; 2013 https://www.omron.com/media/press/2013/05/e0529.html (Year: 2013).*

Han et al.—UWB Radar for Non-contact Heart Rate Variability Monitoring and Mental State Classification 2019 (Year: 2019).*

International Search Report issued in related Application Serial No. PCT/SG2020/050478 on Nov. 9, 2020.

Lazaro A. et al., "Techniques for Clutter Suppression in the Presence of Body Movements during the Detection of Respiratory Activity through UWB Radars." Sensors, Feb. 28, 2014, vol. 14, No. 2, pp. 2595-2618 [Retrieved on Oct. 26, 2020] <DOI: 10.3390/S140202595> Section 1.

* cited by examiner

NON-CONTACT AND NON-INTRUSIVE CONTINUOUS MONITORING PLATFORM

RELATED APPLICATIONS

The subject application is a U.S. National Stage application of International Application No. PCT/SG2020/050478, filed on 18 Aug. 2020. The contents of which is herein incorporated by reference in its entirety.

FIELD OF THE INVENTION

This invention relates to a system and a method for non-contact, non-intrusive and continuous monitoring and predicting clinical outcomes or episodes of subjects in a healthcare institution.

PRIOR ART

Different equipment or assessment in healthcare institutions are essential, to measure and monitor subject's clinical wellbeing when the subject is on the bed, for example temperature, respiratory rate, activity, sleep, rehabilitation progress, cardiac arrest, death, pain. Although essential, the measurement methods are tedious and cumbersome, non-continuous and requires healthcare professionals to manually record equipment measurement readings and make their own manual assessment, followed by clinical assessment based on the available variety of such information.

In hospitals and nursing homes, patients and residents warded are monitored by healthcare professionals but on irregular basis because of the limitations in monitoring equipment, methodology and manpower constraints. Existing monitoring solutions are not ideal for the reasons such as: (i) lacking features needed for a specific monitoring; (ii) privacy concerns; (iii) disruption of patient rest and wellbeing for continuous monitoring; and (iv) obstruction to nursing procedure. Therefore, subject's wellbeing cannot be comprehensively and continuously monitored due to the lack of ability and inaccuracy of data involved. No single device or platform can perform multiple measurement or monitoring, such as respiratory rate measurement, temperature measurement, sleep quality monitoring, patient activity etc. in a continuous, non-contact and non-intrusive basis.

Therefore, those skilled in the art are striving to provide an improved system and method for monitoring subjects that is non-contact basis and continuously

SUMMARY OF THE INVENTION

The above and other problems are solved and an advance in the art is made by a system and method in accordance with this invention. To circumvent the above limitations, the invention is designed based on three basic principles of (i) non-contact; (ii) non-intrusive; and (iii) continuous monitoring. A first advantage of the system and method in accordance with this invention is that the system and method adopt a multi-sensor multi-feature single-device solution, coupled with innovative data collection, storage, detection and analysis to provide customer-centric sense making capability for early warning purposes. The multi-sensor approach enables information collected from different dimensions to complement one-another which in return enables another dimension of intuition and sense making, and at the same time able to achieve the multi-feature capability. A second advantage of the system is that it is adaptive by nature, allowing for further development of features with existing data generated; and future expansion on the platform with new or better sensors. The third advantage is the ability to package the solution as a single device makes it an operationally feasible, cost-effective and attractive solution. The single device is installed on the ceiling facing the bed and its surroundings, and powered by a single Ethernet cable which also serves as a communication channel. The fourth advantage is that finally with the ability to obtain continuous and uninterrupted data, the system is thereby able to describe the current situation of the patient, predict clinical prognosis and lastly prescribe the necessary intervention that will change and improve clinical outcomes.

A first aspect of the invention relates to a monitoring system. The monitoring system comprises a thermal sensor configured to obtain thermal images; an ultra-wideband (UWB) sensor configured to obtain respiratory rate and heart rate measurement; and a processing unit comprising a processor, memory and instructions. The instructions are stored on the memory and executable by the processor to: analyse the thermal images to determine presence of patient on a bed, temperature and activity intensity; and in response to determining presence of patient on the bed and the activity intensity is below a certain threshold, record the temperature, respiratory rate and heart rate.

In an embodiment of the first aspect of the invention, the monitoring system further comprises a heat emitter in a field of view of the thermal sensor configured to provide a constant and stable heat-source.

In an embodiment of the first aspect of the invention, each thermal image is an array of temperature data and the instruction to analyse the thermal images to determine presence of patient on the bed, temperature and activity intensity comprises instructions to: normalise the array of temperature data to approximately human body temperature; process the normalised array of temperature data through a series of image processing techniques including contrast enhancement, brightness enhancement, sharpening of edges; apply object recognition to determine all objects in the thermal image to draw bounding boxes; and in response to determining a first bounding box identified as a human body on the bed, record temperature of patient using bounding box identified as head of the human body.

In an embodiment of the first aspect of the invention, the instruction to record temperature of patient using bounding box identified as head of the human body further comprises instruction to determine activity intensity by comparing value changes of the array of temperature data within a bed boundary from a first thermal image to subsequent thermal images.

In an embodiment of the first aspect of the invention, the instruction to analyse the thermal images to determine presence of patient on a bed, temperature and activity intensity further comprises instruction to determine potential clinical events.

In an embodiment of the first aspect of the invention, the instruction to determine potential clinical events comprises instructions to: perform a look up in a first data structure comprising a list of potential clinical events where each potential clinical events has certain conditions; and in response to all conditions in one of the potential clinical events being satisfied, activate a corresponding alert.

In an embodiment of the first aspect of the invention, the conditions for one of the potential clinical events include presence of patient on the bed, no movement of patient and no respiratory rate and/or heart rate.

A second aspect of the invention relates to a clinical system. The clinical system comprises a plurality of monitoring systems according to the first aspect of the invention and a server comprising a processor, a memory and instructions stored on the memory and executable by the processor to: receive data from the processing unit of the monitoring system; and store the data according to identification number and respective bed and ward information.

In an embodiment of the second aspect of the invention, the instructions of the server further comprise instructions to: perform a look up in a second data structure comprising a list of potential clinical events and recovery conditions where each potential clinical events and recovery conditions has certain conditions; and in response to all conditions in one of the potential clinical events and recovery conditions being satisfied, activate a corresponding course of action.

In an embodiment of the second aspect of the invention, the conditions for one of the potential clinical events and recovery conditions include activity intensity being above a certain threshold for a predetermined number in consecutive number of nights.

A third aspect of the invention relates to a method of monitoring a patient. The method comprises: obtaining thermal images from a thermal sensor; obtaining respiratory rate and heart rate measurement from an ultra-wideband (UWB) sensor; analysing the thermal images to determine presence of patient on a bed, temperature and activity intensity; and in response to determining presence of patient on the bed and the activity intensity is below a certain threshold, record the temperature, respiratory rate and heart rate.

In an embodiment of the third aspect of the invention, the method further comprises obtaining a constant and stable heat-source from a heat emitter placed in a field of view of the thermal sensor.

In an embodiment of the third aspect of the invention, each thermal image is an array of temperature data and the step of analysing the thermal images to determine presence of patient on the bed, temperature and activity intensity comprises: normalising the array of temperature data to approximately human body temperature; processing the normalised array of temperature data through a series of image processing techniques including contrast enhancement, brightness enhancement, sharpening of edges; applying object recognition to determine all objects in the thermal image to draw bounding boxes; and in response to determining a first bounding box identified as a human body on the bed, recording temperature of patient using bounding box identified as head of the human body.

In an embodiment of the third aspect of the invention, the step of recording temperature of patient using bounding box identified as head of the human body further comprises determining activity intensity by comparing value changes of the array of temperature data within a bed boundary from a first thermal image to subsequent thermal images.

In an embodiment of the third aspect of the invention, the step of analysing the thermal images to determine presence of patient on a bed, temperature and activity intensity further comprises determining potential clinical events.

In an embodiment of the third aspect of the invention, the step of determining potential clinical events comprises instructions to: performing a look up in a first data structure comprising a list of potential clinical events where each potential clinical events has certain conditions; and in response to all conditions in one of the potential clinical events being satisfied, activating a corresponding alert.

In an embodiment of the third aspect of the invention, the conditions for one of the potential clinical events include presence of patient on the bed, no movement of patient and no respiratory rate and/or heart rate.

In an embodiment of the third aspect of the invention, the method of monitoring the patient further comprises: performing a look up in a second data structure comprising a list of potential clinical events and recovery conditions where each potential clinical events and recovery conditions has certain conditions; and in response to all conditions in one of the potential clinical events and recovery conditions being satisfied, activating a corresponding course of action.

In an embodiment of the third aspect of the invention, the conditions for one of the potential clinical events and recovery conditions include activity intensity being above a certain threshold for a predetermined number in consecutive number of nights.

BRIEF DESCRIPTION OF THE DRAWINGS

The above advantages and features in accordance with this invention are described in the following detailed description and are shown in the following drawings.

DETAILED DESCRIPTION

This invention relates to a system and a method for non-contact, non-intrusive and continuous monitoring and predicting clinical outcomes or episodes of subjects in a healthcare institution.

This invention relates to a solution that combines different sensors to collect data from a single device. Specifically, the invention relates to a non-contact, non-intrusive and continuous solution that is applicable in a healthcare institution environment for a subject to be monitored on or around a bed. Since the system is non-contact, non-intrusive and continuous, patients can be monitored without compromising patient comfort and without obstructing nursing operations. Furthermore, clinical parameters can be measured and/or derived to describe the existing condition, predict and prescribe interventions that can improve clinical outcomes.

It is envisioned that a system and method in accordance with embodiments of this invention may be used to predict and prescribe interventions that can improve clinical outcomes. The system and method comprises 2 parts, namely, collection and analysis.

The collection part comprises non-contact sensors or wireless devices that can be implemented directly to the invention to obtain information of a monitored subject and the environment. It should be noted that the invention is sensor-agnostic, thus adaptive for future expansion when such data collection sensing devices are available.

The analysis part is based on machine learning models trained to pick up sequences of observable data that correlate to high probability of certain resulting outcomes. The collected data is then processed in real-time by the invention for the purpose of predicting clinical outcomes based on certain sets of actions being determined. These processes are adaptive and can be easily customised according to requirements. A detailed description of the system and/or method in accordance with embodiments of this invention will now be described as follows.

Figure 1:
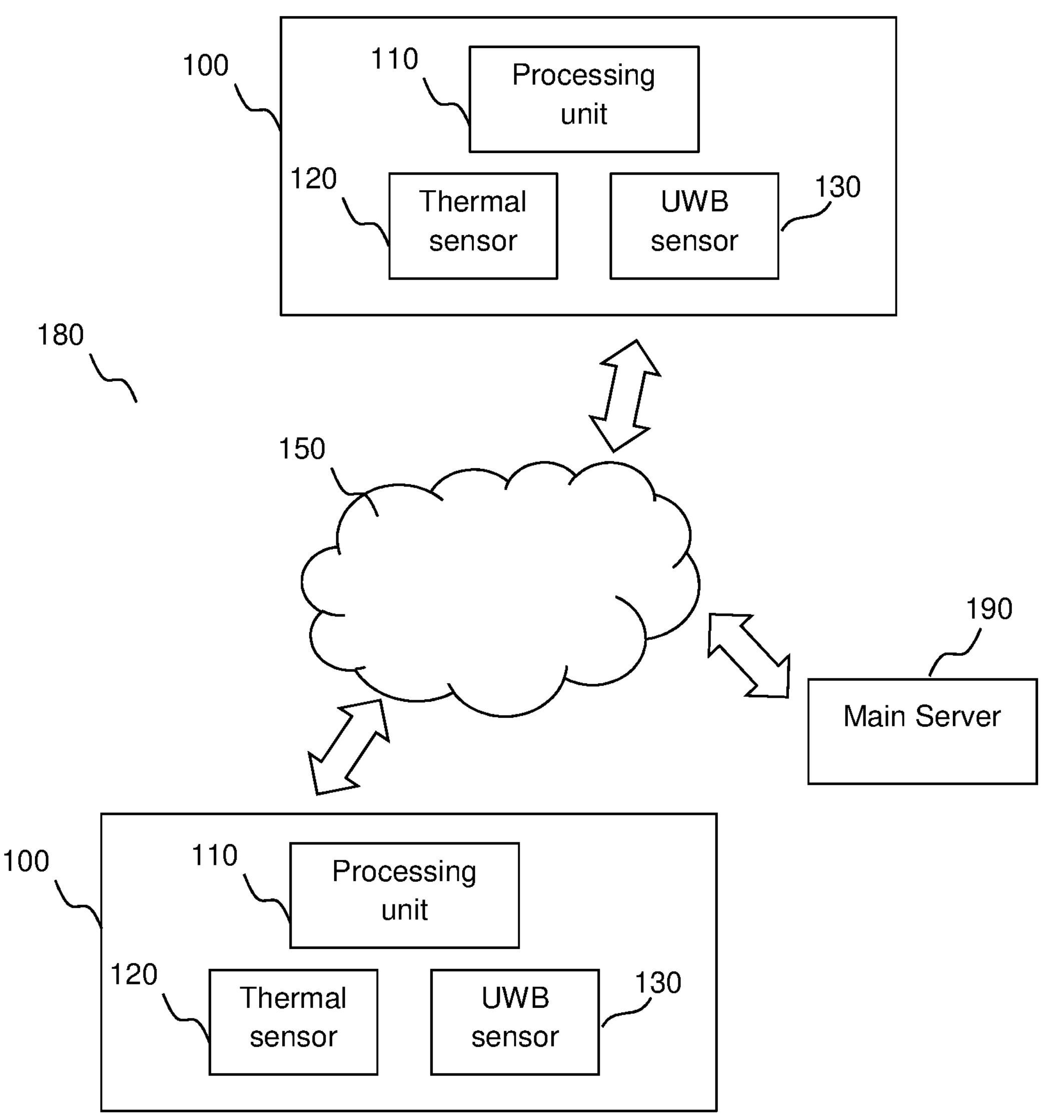
FIG. 1 illustrating an overview of the system for performing the processes in accordance with an embodiment this invention.

FIG. 1 illustrates an overview of a clinical monitoring system 180 comprising monitoring systems 100 for performing the processes in accordance with an embodiment of this invention. The monitoring system 100 comprises, but not limited to, a processing unit 110, a thermal sensor 120 and an ultra-wideband (UWB) sensor 130. One skilled in the art will recognise that other sensors may be added to the monitoring system 100 to obtain different data of a subject being monitored and the selection of other sensors to be incorporated to the monitoring system 100 is left to those skilled in the art.

The thermal sensor 120 and ultra-wideband (UWB) sensor 130 are non-contact sensors for obtaining information on a monitored subject. Each of these sensors is communicatively connected to the processing unit 110. Data is fed through pre-trained machine learning models in the onboard processing unit 110 or main server 190 for analysis and raising of alarm if nursing intervention is needed. Information received from the sensors are transmitted to the main server 190 by the processing unit 110 via a network 150 for storage, report generation and analyses requiring additional processing power.

Figure 2:
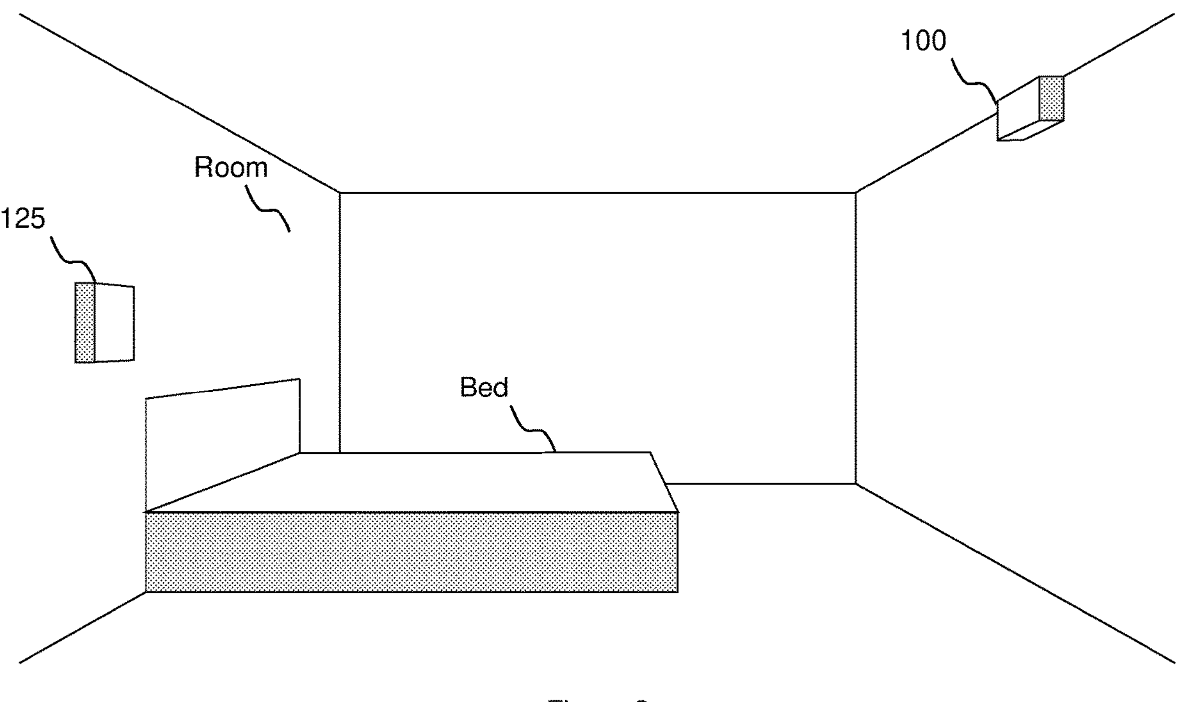
FIG. 2 illustrates the placement of the invention deployed in a typical patient room for performing processes to provide a system in accordance with an embodiment this invention.

The monitoring system 100 is installed in a room to monitor one or more subjects at one time as shown in FIG. 2. The monitoring system 100 is arranged directly above and in front of a bed such that the thermal sensor 120 and UWB sensor 130 have direct line of sight or sensing path of a subject resting on the bed. This ensures that thermal sensor 120 and UWB sensor 130 are capturing information of the subject resting on the bed without obstruction. The combination of the thermal sensor 120 and ultra-wideband (UWB) sensor 130 enables the system to operate continuously regardless of brightness, in the sense that no compensation or switching of sensor or algorithms are required due to changes in environmental lighting conditions. This ensures performance of the monitoring system 100 is maintained and no compromise is made, which is an essential requirement in healthcare monitoring. The placement of the monitoring system 100 at an angle as opposed to directly above or at other height level was extensively evaluated through studies in actual operating wards with real patients. Directly above the bed has its own benefits but is not operationally feasible due to existing ceiling fans and lighting fixtures. Moreover, observing movement directly above the bed prevents any information on height, and especially when a nurse is bending over the patient to perform a procedure. Placing the single device solution at eye-level or below will result in people moving around obscuring the view of the patient easily, and might confuse the system in recognising people incorrectly. Placing the single device solution on the opposite end of the wall/corner ceiling above the head of the bed will have obscured view whenever the bed is tilted upright for the patient to be in a sitting position. Placement of sensors on the side prevents information on the other side of the bed from being identified. Placing of multiple sensors will perform better in terms of accuracy but is infrastructurally challenging and not possible in open wards as long as there are two beds side-by-side. The monitoring system 100 provides a three-dimensional view and consequentially an understanding on both height and placement of objects of people, bed and its environment.

Experiments were conducted with the monitoring system 100 positioned at a height of about 260 cm from floor, and 100 cm away from the foot of the bed. However, as hospitals and nursing homes have different floor-to-ceiling height and furnishing such as a ceiling-mounted TV, absence of air-conditioner, etc., the exact position of the monitoring system 100 with reference to the bed may vary. Performance can be optimised by data collection in the new settings using a combination of methods such as fine-tuning distance thresholds between recognised objects such as distance between a nurse and a patient in relation to the bed, or adjusting the model used to recognise objects due to slight changes due to the view of the sensor placement. Performance of the monitoring system 100 can also be optimised by changing the sensor resolution or lens.

In order to monitor a number of subjects, multiple monitoring system 100 can be installed for each hospital bed to monitor their respective subjects, the surrounding activities and the environment concurrently. Network 150 allows individual monitoring system 100 to communicate with one another. At each bed, the processing unit 110 which forms part of the monitoring system 100 may be communicatively connected to a site server or router prior to connecting to the network 150 in order to communicate with the main server 190.

The thermal sensor 120 operates based on infrared thermography or thermal imaging, detecting radiation in the long-infrared range of the electromagnetic spectrum. Thermography makes it possible to observe variations in temperature and with the thermal sensor, images are reconstructed based on the temperature readings collected in a non-contact manner.

By applying image processing and object recognition techniques on the thermal images obtained by the thermal sensor 120, the monitoring system 100 is able to identify the objects having a particular consistent thermal profile, and subsequently identify the person's head and extract the temperature of this head region. A threshold is applied to discard anomalies and outlier temperature readings in the head region to obtain the accurate temperature of the person. The accuracy of temperature measured is maintained by implementing a blackbody emitter 125 placed at a fixed distance away from the thermal sensor 120 and within the thermal sensor 120 field-of-view.

To ensure the accuracy in the real-time person temperature measurement, a constant and stable heat-source in the form of a blackbody emitter 125 is placed at a fixed distance facing the monitoring system 100 and essentially the thermal sensor 120 and within the thermal sensor 120 field-of-view. The blackbody emitter 125 is unaffected by changes in environmental temperature and will always remain at its pre-set temperature. The blackbody emitter is therefore conveniently mounted on the opposite wall above the bed which has an unobstructed view from the thermal sensor 120 field-of-view. This blackbody emitter 125 will appear to the thermal sensor 120 as a constant and stable known temperature. The thermal sensor 120 will take this point as a reference temperature to calibrate all other thermal readings in real-time. This ensures that the temperature points measured by the thermal sensor 120 is accurate and the entire process is automated and non-contact. Temperature readings and images are transmitted to the main server 190 via the processing unit 110 to be used in conjunction with other clinical parameters.

The ability to measure temperature readings of everything within the thermal sensor 120 field-of-view, thermal images can therefore be constructed. Different objects emit infrared energy based on its inherent thermal properties such as the emissivity and surface. These temperature readings form individual pixels in an array format, and when assigned a colour map, and image can be obtained. Regular human body temperature is constant within a tight range of between 36.5° C. to 37.5° C., and is generally higher than any surrounding objects such as bed, chair, and blanket in order for the human to be comfortable. This allows the sensor to always obtain a human silhouette based on the heat signature of the human, in addition other objects. Key information that could be generated includes: the number of persons within view; the position of the persons in relation to the surrounding; the direction of movement; body postures that indicate if one is standing up, walking, sitting or lying down, and actions such as bed turning, cleaning, medication adherence.

The thermal sensor 120 captures a set of raw data for every frame. The raw data exists as an array of temperature values in a 384×288 matrix. One skilled in the art will recognise that the 384×288 matrix is dependent on the resolution of the thermal sensor used. If a higher or lower resolution is implemented, the size of the matrix would be adjusted accordingly. For purposes of this description, we have indicated a 384×288 matrix as experiments have been conducted based on this resolution. This matrix can be exploited over and over again to facilitate different use cases. Thus, the data collection method is a one-time effort. Depending on the use cases, the same data collected can used differently to obtain different information and as such, the scalability and multi-feature development potential is huge.

The ultra-wideband (UWB) sensor 130 emits electromagnetic pulses from a transmitter and the receiver samples the reflected energy. The UWB sensor 130 is able to sense human presence by detecting any motion as a person is moving across the UWB sensor 130 field-of-view or moving body parts such as hands, head, and legs. The UWB sensor 130 has the ability to sense respiration movement if the human is not moving significantly. After digital signal processing, the UWB sensor 130 outputs the data to the processing unit 110 for further analysis.

The usage of a UWB sensor 130 for respiratory rate and heart rate measurement has limitations. Data from a UWB sensor 130 can only tell if there are movement or otherwise. Thus, the UWB sensor 130 alone has limited real-life applications. This can be improved by coupling the information from the UWB sensor 130 with the information obtained from the thermal sensor 120. For example, processes are implemented to first determine presence of a patient on the bed with or without movement by the thermal sensor 120. If it is determined that the patient is on the bed and not moving, the data obtained from the UWB sensor 130 that is generated as respiratory rate and heart rate whilst patient is not having excessive movement, would be of high confidence levels and of clinically relevance. If the patient is verified via thermal sensor 120 and object recognition techniques to be on the bed, yet the UWB sensor 130 does not pick up any respiration readings, monitoring system 100 will trigger the alarm for the nurse to intervene and check on the patient. This ensures that respiratory rate and heart rate obtained from the UWB sensor 130 is accurate, real-time, automated and non-contact and makes sense clinically and operationally. Respiratory rate and heart rate readings are collected and transmitted to the main server 190 via the processing unit 110 to be used in conjunction with other clinical parameters for recording.

The processing unit 110 is a typical processing system such as an edge computing system, a desktop computer, laptop computer, or other computer terminal capable of handling large data storage and processing need. Processing unit 110 is communicatively connected to network 150 via either a wired or wireless connection to retrieve data from main server 190 and/or site server/router. One skilled in the art will recognise that more than one server 190 may be used without departing from the invention. Further details of the processing unit 110 will be described below with reference to FIG. 3.

Figure 3:
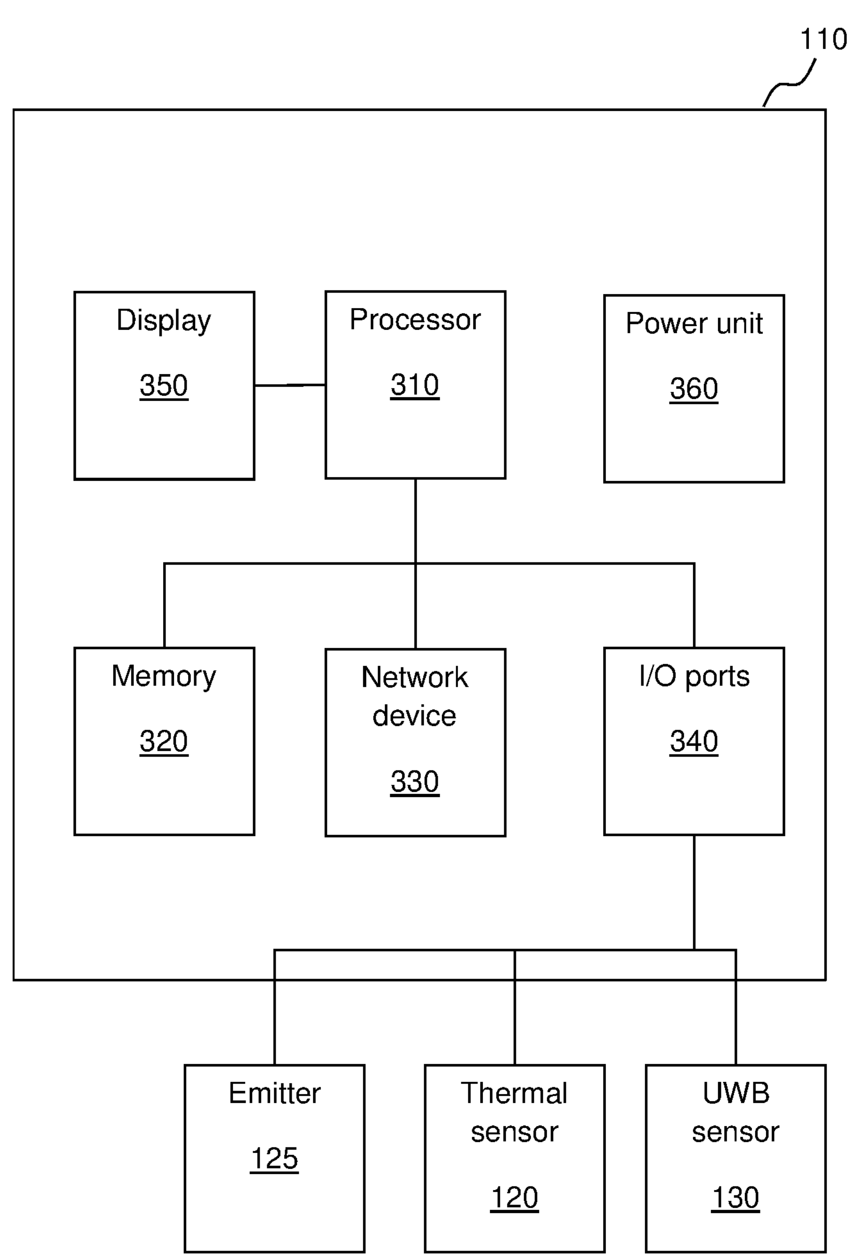
FIG. 3 illustrating a block diagram of the processing unit for performing processes in accordance with an embodiment of this invention.

FIG. 3 illustrates the block diagram of the processing unit 110. The processing unit 110 can receive and transmit data, execute software applications. The processing unit 110 comprises a processor 310, memory 320, network device 330, input/output ports 340, display 350 and power unit 360.

The processor 310 is a processor, microprocessor, microcontroller, application specific integrated circuit, digital signal processor (DSP), programmable logic circuit, or other data processing device that executes instructions to perform the processes in accordance with the present invention. The processor 310 has the capability to execute various applications that are stored in the memory 320.

The memory 320 may include read-only memory (ROM), random-access memory (RAM), electrically erasable programmable ROM (EEPROM), flash cards, or any memory commonly used for computers.

Network device 330 connects processor 310 to a network for transmission of data to and from other processing systems such as the main server 190. In one embodiment where site server or router is provided, network device 330 may be a low power long range wireless transmission module. In order to achieve low power consumption, the network device 330 is communicatively connected to a site server or router instead of directly to the main server 190. In order words, the processing unit 110 is configured to only obtain data from the sensors and transmit the data to the main server 190 via the site server or router.

One or more input/output (I/O) ports 340 can be configured to allow the processor 310 to communicate with and control from various I/O devices. Peripheral devices that may be connected to processing unit 110 via the I/O ports 340 include a USB storage device, an SD card or other storage device for transmitting information to or receiving information from the processing unit 110. In addition to updating applications stored on memory 320 or installing new applications onto the memory via the network device 330, a user may alternatively install new applications or update applications on the memory 320 through a user interface such as a USB via the I/O ports 340. I/O ports 340 also include necessary connectors to connect to a plurality of sensors for receiving data pertaining to the monitored subject. This includes the thermal sensor 120, UWB sensor 130 and the blackbody emitter 125.

Display 350 receives display data from processor 310 and display images on a screen for a user to see. The processing unit 110 is powered by the power unit 360.

One skilled in the art will recognise that other features may be included in the processing unit 110. Further, the components in processing unit 110 may be replaced by other components that perform similar functions. In brief, the processing unit 110 as shown in FIG. 3 is considered merely illustrative and non-limiting.

Essentially, the processing unit 110 is a multi-input data acquisition module that receive pertinent information on the monitored subject. The thermal sensor 120 and UWB sensor 130 are connected to processing unit come with an on-board processor that is configured to receive data and transmit data to a main server 190. It is also capable of analysing data received from the sensors to predict clinical outcomes. In an embodiment where multiple monitor systems 100 are installed in one building, a site server may be installed at the building to perform the analysis. This means that a lower cost processing unit 110 can be implemented where data from the sensors are transmitted to the site server to perform the analysis. This reduces the overall cost of implementing multiple monitoring systems 100 in a building.

Processes stored as instructions in a media that are executed by a processing system in main server 190 or site server provide the method and/or system in accordance with this invention. The instructions may be stored as firmware, hardware, or software. The main server 190 includes a processing system such as a Central Processing Unit (CPU). CPU is a processor, microprocessor, or any combination of processors and microprocessors that execute instructions to perform the processes in accordance with the present invention. The main server 190 further includes memory such as a non-volatile memory such as a Read Only Memory (ROM) and/or volatile memory such as Random Access Memory (RAM). Non-volatile memory stores instructions and data needed to operate various sub-systems and to boot the system at start-up. Volatile memory stores the instructions and data needed by CPU to perform software instructions for processes such as the processes required for providing a system in accordance with this invention. One skilled in the art will recognise that any number of types of memory may be used as volatile memory and the exact type used is left as a design choice to those skilled in the art.

The main server 190 further includes I/O device, keyboard, display, additional memory, network device and any number of other peripheral devices connect with the CPU for use in applications being executed by CPU. I/O device is any device that transmits and/or receives data from CPU. Keyboard is a specific type of I/O that receives user input and transmits the input to CPU. Display receives display data from CPU and display images on a screen for a user to see. Additional memory is a device that transmits and receives data to and from CPU for storing data to a media. Network device connects CPU to a network for transmission of data to and from other processing systems such as the processing unit 110.

One skilled in the art will recognise that the exact configuration of the processing system in the main server 190 or site server may be different and the exact configuration of the processing system in each of the main server 190 and site server may vary without departing from the invention.

A site server may be provided at one site. Advantageously, data from the sensors is backed up on the site database. This prevents loss of data in case of temporary disengagement with the main server 190. A site server is also able to perform some analysis on site. This drastically reduces the workload on the main server 190.

Figure 4:
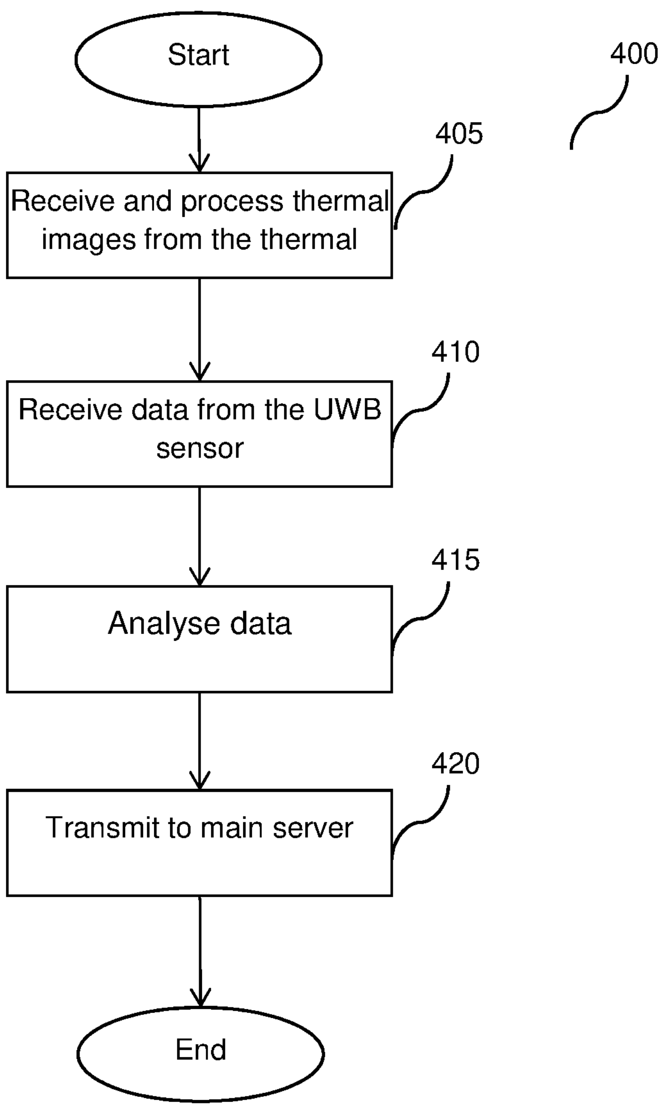
FIG. 4 illustrating a process performed by the processing unit for receiving data from the thermal sensor and UWB sensor in accordance with an embodiment of this invention.

FIG. 4 illustrates a process 400 performed by the processing unit 110 for receiving data from the thermal sensor 120 and UWB sensor 130 in accordance with an embodiment of this invention. Process 400 begins with step 405 by receiving an array of temperature data per frame from the thermal sensor 120, which generates at least five frames per second. This array of temperature data is then processed in the following manner.

1. The array of temperature data is normalised to within a present temperature range, to exclude extreme low and high temperatures and therefore amplify the range of temperature which is of interest, centering around the human body temperature of 36.5° C.
2. The normalised array of temperature data is thereafter processed through a series of image processing techniques including contrast enhancement, brightness enhancement, sharpening of edges.
3. Object recognition is then applied to the processed array of temperature data in the following manner. The array of temperature data is first split into cells in the form of a grid. Each cell is responsible for predicting bounding boxes of potential objects to be recognised and removing boxes with low object probability and matching against a pre-trained model. In order to train a model, a certain number of images are required. Each image includes marked out points and bounding box or boxes with tag depicting a category such as people, hand, leg, torso, head, table, chair, bed, etc. One skilled in the art will recognise that the higher the number of images used may train a more accurate model. However, this number of images would taper off and any further images to train the model will have insignificant improvement or even suffer from over-training. The exact number of images to be used for training a model may be through trial and error and is left to one skilled in the art to determine. Approximately 70-80% of the images are used to train a model while the remaining 20-30% of the images are used to verify the accuracy of the model. Such training of model is well known in the art and hence exact details of training a model and subsequent re-training of the model are omitted for brevity. With the trained model, the objection recognition is able to find all the objects in the image to draw the bounding box. Boxes with highest shared area will be merged to obtain the final object bounding box. The methodology of segmenting an image into grids, and then finding overlaps of parts of a potential object and later merging into a final bounding box is a common methodology and two known examples are the You Only Look Once (YOLO) family algorithms and Single Shot Multibox Detector (SSD).

In this application two bounding box for a human is obtained, the first bounding box encompasses the entire human body and the second bounding box for the head of the human body. The bounding box for the human returns a 1 or 0 and contributes towards counting the total number of people in the thermal sensor 120 field-of-view. The bounding box of the human can also be used to estimate its position in relation to other humans, or with objects such as bed and chair. Sequence of how the bounding box changes in relation to other objects such as the bed, can therefore be an indication of motion into or out of the bed. For example, assuming a particular bounding box which is recognised as a person from one end is entering the room and moving towards the bed, the distance between the bounding box to the bed will reduce over time. We can then deduce that a person is moving towards the bed at certain speed. The bounding box for the head enables the temperature of the person to be measured accurately.

4. Activity intensity is also determined based on the processed array of temperature data within the bed boundary. Since the number of pixels in which the bed covers is within a known boundary, we can monitor the change in value of the pixels due to movement within the boundary of the bed. At any one time, the maximum number of pixels changing as a percentage of the entire bed frame theoretically is 100%, but this is not likely possible unless the entire bed frame has changing temperature values due to movement. Therefore, the activity intensity can be expressed simply as a percentage of movement 0% to 100% (changing pixel values within the bed boundary) or as a ratio 0 to 1.00. By comparing array value changes within the bed boundary from a frame to frame perspective, the motion can be quantified which correlates as activity intensity of the patient on the bed. By knowing there is a single person on the bed through object recognition, it is then possible to know how much the person has moved on the bed in real-time.

In step 410, process 400 receives data from the UWB sensor 130. The raw data is processed internally within the UWB sensor 130 itself to directly output in real time the (a) respiratory rate in breaths per minute (i.e. breaths per minute), (b) confidence level for respiratory rate (automatically determined by the UWB sensor 130), (c) heart rate per minute (i.e. beats per minute), (d) confidence level for heart rate (automatically determined by the UWB sensor 130), and (e) distance between source of movement detected to UWB sensor 130 (i.e. in meters or centimetre). As these information are known processes, the exact details on translating the raw data to the information listed above are omitted for brevity.

In step 415, process 400 analyses the data from steps 405 and 410 to determine the temperature, respiratory rate and heart rate. Specifically, process 400 needs to first determine presence of a patient on the bed with or without movement based on the object recognition in step 405. If it is determined that the patient is on the bed and not moving, the data obtained from the UWB sensor 130 that is generated as respiratory rate and heart rate whilst patient is not having excessive movement (i.e. low activity intensity), would be of high confidence levels and of clinically relevance. For example, process 400 may record the temperate, respiratory rate and heart rate when satisfying the following conditions, object recognition determines a patient is on the bed, activity intensity is below certain threshold and confidence level for respiratory rate and heart rate from UWB sensor is above certain threshold. Concurrently, process 400 also analyses the data from steps 405 and 410 to determine potential clinical events. Specifically, based on the data received from steps 405 and 410, process 400 will perform a look up in a first data structure comprising a list of potential clinical events, i.e. bed exit, shock, continuous movement, etc. Each potential activity has certain conditions and if the data from steps 405 and 410 matches a predetermined number of conditions in one of the clinical events, a corresponding trigger such as an alert will be activated. The alert may be an alarm to the care giver responsible for the patient monitored by the monitoring system 100. For example drastic changes in both respiratory rate, heart rate and temperature indicates clinical deterioration which will automatically trigger an alarm for urgent clinical intervention, thereby predicting clinical events such as septic shock or cardiac arrest. In another example, if the patient is verified via the object recognition to be on the bed but the UWB sensor 130 does not pick up any respiratory rate and/or heart rate, process 400 will trigger the alarm for the nurse to intervene and check on the patient and/or no movement or no activity based on the activity intensity determined. This ensures that respiratory rate and heart rate obtained from the UWB sensor 130 is accurate and real-time. Temperature, respiratory rate and heart rate readings are collected and transmitted to the main server 190 to be used in conjunction with other clinical parameters for recording. The first data structure can be customised to detect and/or monitor for various abnormalities and to work with a myriad type of alarm triggering protocol that will facilitate easy customisation to meet different operating scenario without any change in hardware.

In step 420, the data processed from step 405, 410 and analysed data and activity intensity are transmitted to the main server 190 for further analysis. The data includes number of people, respiratory rate, heart rate, temperature of patient, thermal images, bed-exit status, and activity intensity.

Process 400 ends after step 420.

Figure 5:
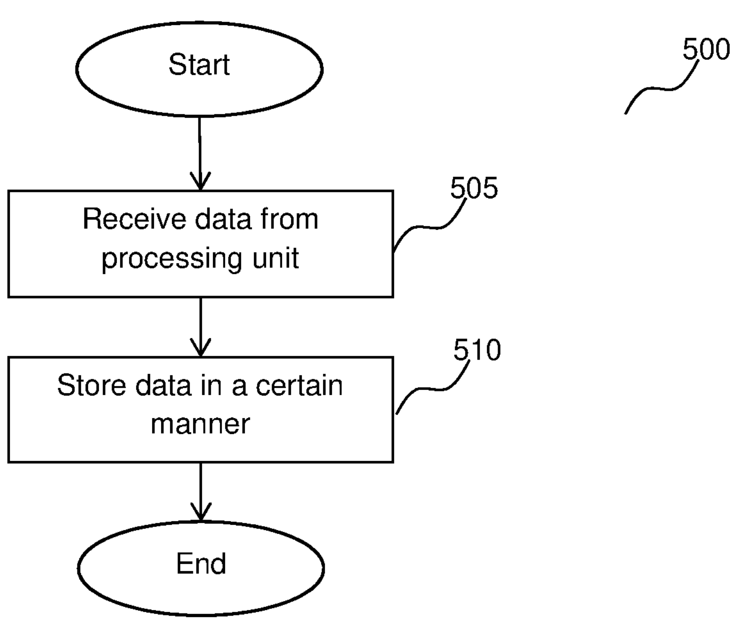
FIG. 5 illustrating a process performed by a main server or a site server to store data received from the processing unit in accordance with an embodiment of this invention.

FIG. 5 illustrates a process 500 performed by the main server 190 or a site server in accordance with an embodiment of this invention. Process 500 begins with step 505 by receiving the data from the processing unit 110.

In step 510, in response to receiving the data from the processing unit 110, process 500 stores the data according to the identity of the patient. The data is saved according to monitoring system 100 identification number, and its respective bed and ward information to distinguish monitoring system 100 from one another.

Figure 6:
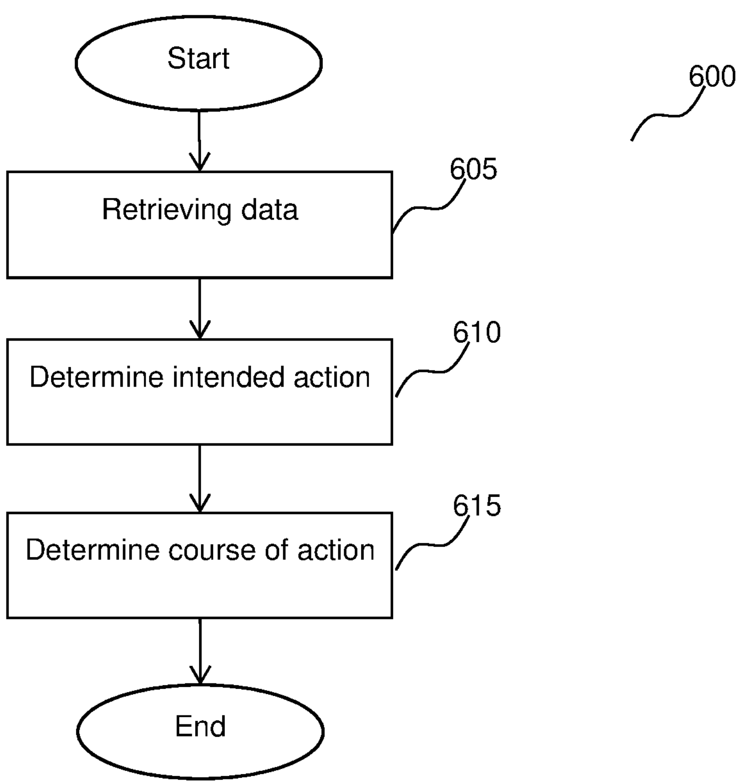
FIG. 6 illustrating a process performed by the main server or the site server to analyse the data received from the processing unit in accordance with an embodiment of this invention.

FIG. 6 illustrates a process 600 performed by the main server 190 or a site server to analyse the data in accordance with an embodiment of this invention. Process 600 begins with step 605 by retrieving data of a patient.

In step 610, the physiological and activity intensity parameters are retrieved and analysed based on historical data comparison. A second data structure comprising a list of potential clinical events and recovery conditions, i.e. sleep quality, nocturnal activity, recovery status, etc. Each potential clinical event or recovery condition has certain requirements and if the physiological and activity intensity parameters matches all the requirements in one of the potential clinical event or recovery condition, a corresponding course of action will be activated. The course of action may be sent to the care giver responsible for the patient monitored by the monitoring system 100 via a message, a notification via a mobile application or an email. Analysis of respiratory rate, heart rate and activity intensity over prolonged periods provide accurate depiction of sleep quality and nocturnal activity. Typically, the doctor will do their ward rounds once or twice a day. At the bedside, they will then look at whatever data is available i.e. the temperature, respiratory rate, heart rate, blood pressure data that had been collected throughout the previous day usually on a 4 hourly or 6 hourly basis, and they will ask the nurse or the patient how their sleep had been, or ask whether they are in pain, and make decisions based on these input. For respiratory rate and heart rate, they are never accurate, due to the nature of how they are collected. Asking the patient how much they have slept is also not inaccurate. The data collection in accordance with this invention ensures that data obtained is independent of human biases, accurate, consistent and quantifiable format which allows the clinicians better insights on the actual condition of the patient. In short, this is a data driven analysis. Sleep (nocturnal activity) over a longer period is especially important, for example, lack of sleep which means higher nocturnal activity at night will result in slower recuperation and recovery, higher risk of delirium, agitation. Such analysis can then aid clinicians to understand the recovery status of the patients and whether medication can aid them in getting better rest and thereby recover much quickly. Additionally, activity intensity when tracked over prolonged periods indicates the rehabilitation progress of post-surgical patients. This can be tracked by activity monitoring intensity being above a certain threshold for a predetermined number in consecutive number of nights. When compared with historical data, the rehabilitation progress can be predicted, in addition to the predicted length of inpatient stay. This information is then used to feedback to both patient and clinicians, including physiotherapists and occupational therapists, to improve rehabilitation outcomes. Healthcare institution also uses this information to plan for bed-turnaround time and better manage operations. The second data structure can be customised to detect and/or monitor for various clinical events and recovery conditions and to work with a myriad type of alarm triggering protocol that will facilitate easy customisation to meet different operating scenario without any change in hardware.

In step 615, process 600 determines a relevant course of action based on the determined potential clinical events and recovery conditions using the second data structure.

One skilled in the art will recognise that various features can be developed and added on a stackable, modular fashion where only the executables are required to be run on real time on edge. The current monitoring system 100 comprises of two sensors—the thermals sensor 120 and the UWB sensor 130. When necessary and available, monitoring system 100 can have additional sensors such as an optical Red-Green-Blue (RGB) sensor, depth sensor, Radio Frequency Identification (RFID) sensor. As the main computing is done on the monitoring system 100 itself, specifically the processing unit 110, this eliminates extensive and heavy computing power that is traditionally required on the main server. This enables the solution to be easily scaled up and not restricted to infrastructural limitations in computing power.

A first use case of the invention is in the hospital setting where patients are monitored round the clock for bed-exit intentions. By predicting the intention of high fall risks patients trying to get out of bed unassisted, timely intervention can be triggered to help the patient, thereby eliminating the possibility of them getting into dangerous positions. In so doing, falls that may happen as a result is eradicated completely.

Inpatient falls are common yet complex challenges that influence hospital care, particularly in elderly patients. More than one-third of inpatient falls results in injury, such as fractures and head trauma, resulting in heavy burden in terms of medical, financial and social outcomes. Falls that do not result in injury may consequently cause distress and anxiety to patients, next-of-kin and healthcare team, and may lead to restriction of future activity, further losses of strength and lastly independence. Traditional solutions such as bed-exit sensor mats or motion detectors are too inaccurate and are cumbersome to deploy with no automation or smart features. Nurses usually suffer from alarm fatigue and end up shelfing such technologies. Furthermore traditional solutions are on a detection basis which means they detect a bed-exit. This invention predicts the intention by the patient to exit the bed, thereby providing nurses sufficient time to intervene.

The above is a description of embodiments of a method and system in accordance with embodiments of this invention. It is foreseeable that those skilled in the art can and will design alternative method and system based on this disclosure that infringe upon this invention as set forth in the following claims.

The invention claimed is:

1. A monitoring system comprising:

a thermal sensor configured to obtain thermal images, wherein each thermal image is a combination of pixels, and each pixel is defined based on an individual temperature reading;

an ultra-wideband (UWB) sensor configured to obtain respiratory rate and heart rate measurement; and a processing unit comprising a processor, memory and instructions stored on the memory and executable by the processor to:

analyse the thermal images to determine a presence of a patient on a bed, and a temperature of the patient on the bed, by normalizing the combination of pixels based on an average human body temperature and processing the normalized combination of pixels through a series of image processing techniques including at least one of: contrast enhancement, brightness enhancement, and sharpening of edges; and compare value changes of the combination of pixels within a predefined boundary from a first thermal image to subsequent thermal images to determine an activity intensity; and in response to determining presence of patient on the bed and the activity intensity is above a first predetermined threshold, record the temperature, respiratory rate and heart rate.

2. The monitoring system according to claim 1 further comprising a heat emitter in a field of view of the thermal sensor configured to provide a constant and stable heat-source.

3. The monitoring system according to claim 1, wherein the instruction to analyse the thermal images to determine presence of patient on the bed and, temperature comprises instructions to:

apply object recognition to determine all objects in the thermal image to draw bounding boxes; and in response to determining a first bounding box identified as a human body on the bed, record temperature of patient using bounding box identified as head of the human body.

4. The monitoring system according to claim 3 wherein the instruction to analyse the thermal images to determine presence of patient on a bed and temperature further comprises instruction to:

determine potential clinical events based on data from both the thermal sensor and the UWB sensor.

5. The monitoring system according to claim 4 wherein the instruction to determine potential clinical events comprises instructions to:

perform a look up in a first data structure comprising a list of potential clinical events where each potential clinical events has certain conditions;

in response to all conditions in one of the potential clinical events being satisfied, activate a corresponding alert.

6. The monitoring system according to claim 5 wherein the conditions for one of the potential clinical events include presence of patient on the bed, no movement of patient and no respiratory rate and/or heart rate.

7. A clinical system comprising a plurality of monitoring systems according to claim 1 and a server comprising a processor, a memory and instructions stored on the memory and executable by the processor to:

receive data from the processing unit of the monitoring system;

store the data according to identification number and respective bed and ward information.

8. The clinical system according to claim 7 wherein the instructions of the server further comprise instructions to:

perform a look up in a second data structure comprising a list of potential clinical events and recovery conditions where each potential clinical events and recovery conditions has certain conditions; and in response to all conditions in one of the potential clinical events and recovery conditions being satisfied, activate a corresponding course of action.

9. The clinical system according to claim 8 wherein the conditions for one of the potential clinical events and recovery conditions include activity intensity being above a second predetermined threshold for a predetermined number in consecutive number of nights.

10. A method of monitoring a patient comprising:

obtaining thermal images from a thermal sensor, wherein each thermal image is a combination of pixels, and each pixel is defined based on an individual temperature reading;

obtaining respiratory rate and heart rate measurement from an ultra-wideband (UWB) sensor;

analysing the thermal images to determine a presence of a patient on a bed and a temperature of the patient on the bed, by normalizing the combination of pixels based on an average human body temperature and processing the normalized combination of pixels through a series of image processing techniques including at least one of: contrast enhancement, brightness enhancement, and sharpening of edges;

comparing value changes of the combination of pixels within a predefined boundary from a first thermal image to subsequent thermal images to determine an activity intensity; and in response to determining presence of patient on the bed and the activity intensity is above a first predetermined threshold, record the temperature, respiratory rate and heart rate.

11. The method of monitoring the patient according to claim 10 further comprising:

obtaining a constant and stable heat-source from a heat emitter placed in a field of view of the thermal sensor.

12. The method of monitoring the patient according to claim 10 wherein-the step of analysing the thermal images to determine presence of patient on the bed and temperature comprises:

applying object recognition to determine all objects in the thermal image to draw bounding boxes; and in response to determining a first bounding box identified as a human body on the bed, recording temperature of patient using bounding box identified as head of the human body.

13. The method of monitoring the patient according to claim 10 wherein the step of analysing the thermal images to determine presence of patient on a bed, temperature and activity intensity further comprises:

determining potential clinical events based on information obtained from both the thermal sensor and the UWB sensor.

14. The method of monitoring the patient according to claim 13 wherein the step of determining potential clinical events comprises instructions to:

performing a look up in a first data structure comprising a list of potential clinical events where each potential clinical events has certain conditions;

in response to all conditions in one of the potential clinical events being satisfied, activating a corresponding alert.

15. The method of monitoring the patient according to claim 14 wherein the conditions for one of the potential clinical events include presence of patient on the bed, no movement of patient and no respiratory rate and/or heart rate.

16. The method of monitoring the patient according to claim 13 further comprising:

performing a look up in a second data structure comprising a list of potential clinical events and recovery conditions where each potential clinical events and recovery conditions has certain conditions; and in response to all conditions in one of the potential clinical events and recovery conditions being satisfied, activating a corresponding course of action.

17. The method of monitoring the patient according to claim 16 wherein the conditions for one of the potential clinical events and recovery conditions include activity intensity being above a second predetermined threshold for a predetermined number in consecutive number of nights.

* * * * *